United States Patent
Koerner et al.

(10) Patent No.: US 9,778,231 B2
(45) Date of Patent: Oct. 3, 2017

(54) ULTRASONIC INSPECTION END EFFECTOR

(71) Applicant: Spirit AeroSystems, Inc., Wichita, KS (US)

(72) Inventors: Kendall F. Koerner, Wellington, KS (US); Adam J. Donar, Prairie Village, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 327 days.

(21) Appl. No.: 14/711,419

(22) Filed: May 13, 2015

(65) Prior Publication Data
US 2016/0334374 A1 Nov. 17, 2016

(51) Int. Cl.
*G01N 29/28* (2006.01)
*G01N 29/04* (2006.01)
*G01N 29/22* (2006.01)
*G01N 29/265* (2006.01)

(52) U.S. Cl.
CPC ........... *G01N 29/28* (2013.01); *G01N 29/043* (2013.01); *G01N 29/225* (2013.01); *G01N 29/265* (2013.01); *G01N 2291/023* (2013.01); *G01N 2291/0231* (2013.01); *G01N 2291/106* (2013.01); *G01N 2291/2694* (2013.01)

(58) Field of Classification Search
CPC .. G01N 29/043; G01N 29/225; G01N 29/265; G01N 29/28; G01N 2291/023; G01N 2291/0231; G01N 2291/106; G01N 2291/2694
See application file for complete search history.

(56) References Cited

U.S. PATENT DOCUMENTS

| | | | | |
|---|---|---|---|---|
| 2,722,636 A | * | 11/1955 | Minchom | G01N 27/9033 324/216 |
| 2,969,671 A | * | 1/1961 | Sproule | G01N 29/0636 73/609 |
| 3,100,987 A | * | 8/1963 | Bincer | G01N 29/2487 73/641 |
| 3,159,756 A | * | 12/1964 | Beaujard | G01N 29/28 310/336 |
| 3,209,582 A | * | 10/1965 | Greenberg | G01N 29/265 310/336 |
| 3,326,037 A | * | 6/1967 | Stewart | G01N 29/265 73/620 |

(Continued)

*Primary Examiner* — David Bolduc
(74) *Attorney, Agent, or Firm* — Hovey Williams LLP

(57) ABSTRACT

A through-transmission ultrasonic (TTU) inspection system for ultrasonic inspection of a part, such as an aircraft component. The TTU inspection system may include a first end effector and/or a second end effector. The first end effector may be positioned on a first surface of the part and the second end effector may be positioned on a second surface of the part, opposite the first surface. The first and/or second end effector may also include an acoustic coupling medium encircled by a plurality of pins independently movable toward and away from a housing of the first and/or second end effector, such that the pins may follow local part contours along the first surface at all times, while retaining the acoustic coupling medium between the first surface and a transducer in the housing of the first and/or second end effector.

20 Claims, 3 Drawing Sheets

(56) References Cited

U.S. PATENT DOCUMENTS

| | | | | |
|---|---|---|---|---|
| 3,585,851 A * | 6/1971 | Walther | G01N 29/0609 | 73/624 |
| 3,895,685 A * | 7/1975 | Gillette | B41J 2/285 | 181/0.5 |
| 4,237,901 A * | 12/1980 | Taenzer | A61B 8/4281 | 600/443 |
| 4,285,243 A * | 8/1981 | Collingwood | G01N 29/265 | 73/623 |
| 4,375,165 A * | 3/1983 | de Sterke | G01N 29/265 | 73/622 |
| 4,429,577 A * | 2/1984 | Sorenson | A61B 8/4281 | 310/336 |
| 4,454,764 A * | 6/1984 | Sorenson | G01N 29/28 | 310/336 |
| 5,046,364 A * | 9/1991 | Stasuk | G01B 17/02 | 73/623 |
| 5,426,980 A * | 6/1995 | Smith | G01N 29/069 | 73/632 |
| 5,460,046 A * | 10/1995 | Maltby | G01N 29/09 | 73/623 |
| 5,479,099 A * | 12/1995 | Jiles | G01R 33/12 | 324/222 |
| 5,913,243 A * | 6/1999 | Hopeck | G01N 29/223 | 73/644 |
| 6,298,727 B1 * | 10/2001 | Fleming | G01N 29/22 | 73/642 |
| 6,481,290 B1 * | 11/2002 | MacInnis | G01N 29/11 | 73/644 |
| 6,577,391 B1 * | 6/2003 | Faupel | A61B 5/0059 | 356/337 |
| 6,975,899 B2 * | 12/2005 | Faupel | A61B 5/0071 | 600/407 |
| 9,121,817 B1 * | 9/2015 | Roach | G01N 29/28 | |
| 2004/0177681 A1 * | 9/2004 | Harthorn | E21B 17/01 | 73/152.57 |
| 2008/0315871 A1 * | 12/2008 | Lepage | G01N 27/9013 | 324/242 |
| 2009/0049920 A1 * | 2/2009 | Young | G01N 29/07 | 73/649 |
| 2009/0277269 A1 * | 11/2009 | Sarr | G01N 29/07 | 73/620 |
| 2010/0024559 A1 * | 2/2010 | Bossi | G01N 29/043 | 73/644 |
| 2011/0072905 A1 * | 3/2011 | Lam | G01N 29/221 | 73/622 |
| 2011/0178727 A1 * | 7/2011 | Hafenrichter | G01M 5/0016 | 702/38 |
| 2013/0283918 A1 * | 10/2013 | Habermehl | G01N 29/26 | 73/622 |
| 2013/0289766 A1 * | 10/2013 | Hafenrichter | B25J 9/02 | 700/245 |
| 2014/0305216 A1 * | 10/2014 | Hafenrichter | G01N 29/07 | 73/598 |
| 2014/0305220 A1 * | 10/2014 | Fetzer | G01N 29/262 | 73/629 |
| 2014/0377450 A1 * | 12/2014 | Knorr | G01B 17/025 | 427/9 |
| 2015/0367586 A1 * | 12/2015 | Georgeson | B06B 1/0688 | 367/140 |

* cited by examiner

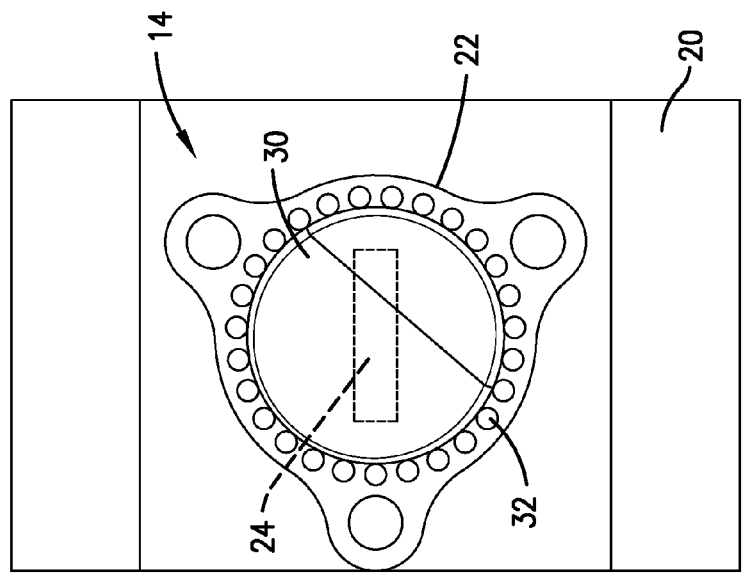
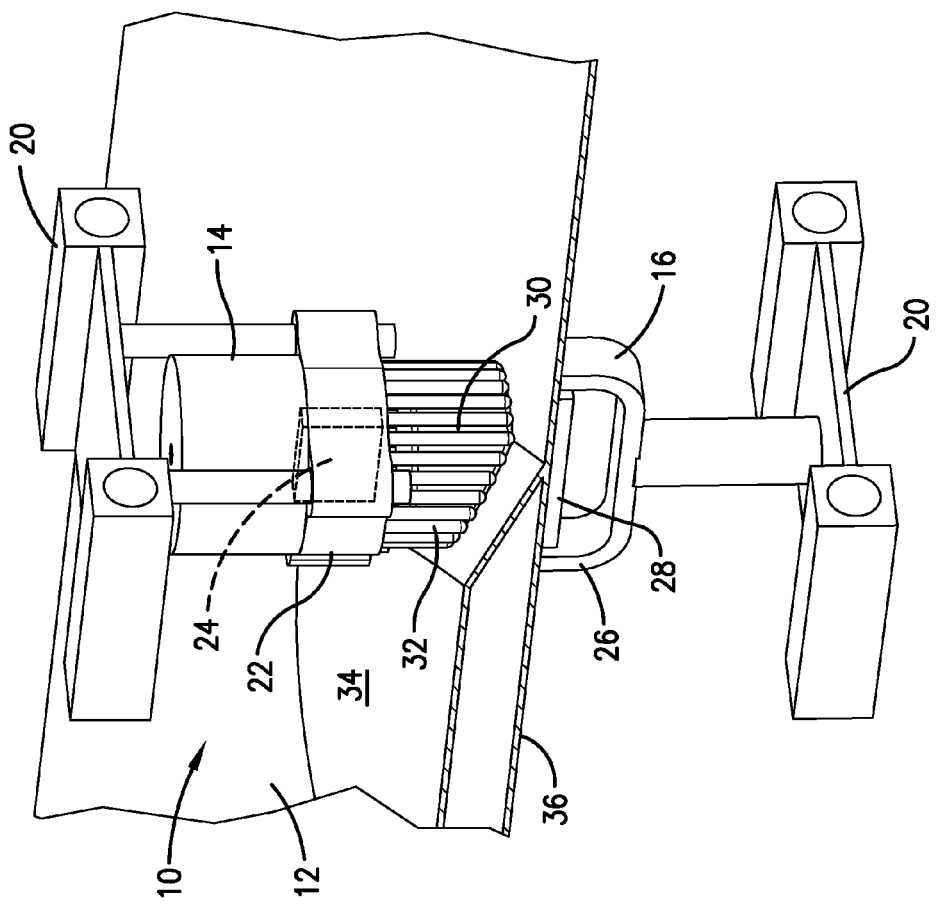
Fig. 3.
Fig. 2.

ULTRASONIC INSPECTION END EFFECTOR

BACKGROUND

Commercial airplanes and components thereof are increasingly being manufactured from composite materials that may require ultrasonic inspection to determine part integrity. In order to perform an ultrasonic inspection, a transducer that transmits and/or receives sound waves must be acoustically coupled to the part. Water or some other liquid is typically disposed between the transducer and the part to be inspected to provide a medium through which sound waves can travel.

Inspection may be performed from one side (i.e., pulse-echo inspections) or from two sides, referred to herein as the through-transmission (TTU) method. The one side, pulse-echo inspection method is not effective on honeycomb core sandwich panels, so the TTU method is needed to inspect such structures. In addition, the TTU method may provide a more detailed assessment of the condition of a part than other methods. For example, TTU inspection can be used to quantify the amount of porosity present in a composite laminate. A TTU inspection is performed by transmitting sound waves into one side of the part and receiving the sound waves on the opposite side of the part using two transducers coupled to the part simultaneously and on opposite sides.

Challenges may arise when a part to be inspected by the TTU method has only one smooth simple surface, with its opposite surface having complex curvatures and/or out-of-plane features. The transducer coupled to the complex surface must be maintained in angular alignment with the transducer on the simple surface, which may require it to be oriented in a way that deviates from the local surface contour on the complex side. Because of these challenges, some prior art TTU methods require immersing the entire part to be inspected in a tank of coupling fluid, with the transducers positioned far enough from the complex surface to avoid interference with out-of-plane features, while still maintaining acoustic coupling. This solution is inefficient and not practical for large parts.

Alternatively, a squirter system can enable TTU inspection by sending sound waves through moving streams of liquid directed at opposing sides of a part. This approach requires a large amount of liquid to be pumped and recovered, particularly if the transducer is large or an array of transducers is used, as is often the case with inspection of aircraft components. Furthermore, the moving stream of liquid creates splashing that can interfere with transmission of the sound waves.

SUMMARY OF THE INVENTION

Embodiments of the present invention solve the above-mentioned problems and provide a distinct advance in the art of ultrasonic inspection by using at least one adaptable end effector.

One embodiment of the invention may include an ultrasonic inspection system for ultrasonic inspection of a part. The system may include a first end effector and/or a second end effector. The first end effector may include a first housing and at least one transducer fixed to the first housing. The first end effector may also include an acoustic coupling medium cooperatively encircled by a plurality of pins movably coupled to the first housing. In use, the pins may be placed against a surface of the part to be inspected and the transducer may transmit ultrasonic or sound waves through the acoustic coupling medium and the part. The pins may be independently movable toward and away from the first housing, accommodating local variations in surface geometry or out-of-plane features of the part being inspected.

In some embodiments of the invention, a through-transmission ultrasonic (TTU) inspection system for ultrasonic inspection of a part is provided. The TTU inspection system may include a first end effector and/or a second end effector. The first end effector may have a first housing and a transducer fixed to the first housing for transmitting or receiving ultrasonic waves. The second end effector may have a second housing and a transducer fixed to the second housing for transmitting or receiving ultrasonic waves. The first end effector may also include an acoustic coupling medium and a plurality of pins independently movable into and out of the first housing. The pins may each be spaced apart from each other and may cooperatively encircle the acoustic coupling medium, forming a fence for retaining the acoustic coupling medium.

Another embodiment of the invention is a method for inspecting a part having a first surface and a second surface opposite of the first surface using through-transmission ultrasonic (TTU) inspection. The method may include the steps of placing a first end effector against the first surface of the part and placing a second end effector against the second surface of the part in alignment with the first end effector. The first end effector may include a first housing and an array of transducers fixed to the first housing for transmitting or receiving ultrasonic waves. The second end effector may include a second housing and an array of transducers fixed to the second housing for transmitting or receiving ultrasonic waves. Next, the method may include transmitting ultrasonic waves with the transducers of the first end effector and receiving ultrasonic waves with the transducers of the second end effector. Either the first and/or second end effectors may additionally include an acoustic coupling medium and a plurality of pins cooperatively encircling the acoustic coupling medium. The acoustic coupling medium may include a bag, pouch, or balloon with a liquid, flowable solid, elastomer material, or gel retained therein. The pins may be independently movable into and out of the first or second housing, each spaced a small distance apart from each other to form a fence retaining the acoustic coupling medium.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein:

FIG. 2 is a cross-sectional perspective elevation view of the TTU inspection system of FIG. 1;

FIG. 3 is a bottom plan view of the end effector of FIG. 1; and

Figure 1:
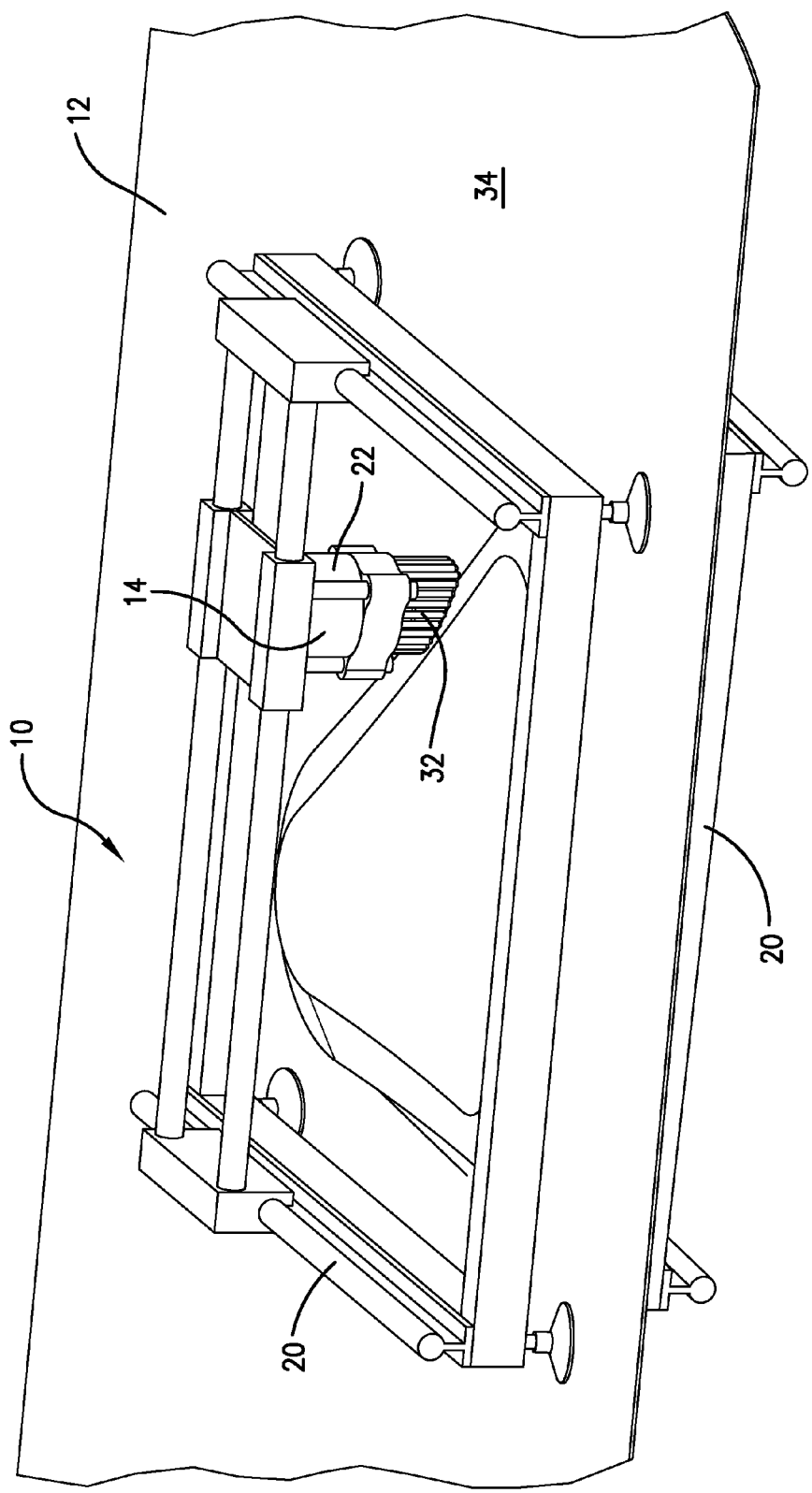
FIG. 1 is a top perspective view of a through-transmission ultrasonic (TTU) inspection system with a transducer having an adapted end effector constructed according to embodiments of the present invention.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

A through-transmission ultrasonic (TTU) inspection system 10 constructed in accordance with embodiments of the present invention is illustrated in FIGS. 1-3. The system 10 is configured for ultrasonic inspection of a part 12. The part 12 may be any component requiring ultrasonic inspection, such as an aircraft component, nacelle wall, honeycomb panel, and the like. The part may have a first surface 34 and a second surface 36 opposite of the first surface 34. The system 10 may include a first end effector 14, a second end effector 16, and a plurality of actuation and support components 20.

In some embodiments of the invention, at least some of the actuation and support components 20 may be controlled by a programmed processor, microcontroller, related circuitry, and the like. However, manual actuation of the first and/or second end effectors 14, 16 may be used without departing from the scope of the invention. Data received by the end effectors 14, 16 may also be sent to a programmed processor, microcontroller, related circuitry, memory, databases, cloud storage devices, and the like.

As illustrated in FIGS. 2 and 3, the first end effector 14 may comprise a first housing 22 and a first transducer 24 fixed to the first housing 22. Likewise, the second end effector 16 having a second housing 26 and a second transducer 28 fixed to the second housing 26, as illustrated in FIG. 2. The first and second transducers 24,28 may each comprise one or more transducers configured to transmit and/or receive sound waves or ultrasonic waves to and from each other. For example, the transducers 24,28 may include linear arrays of transducers arranged in any configuration, such as a plurality of rows and/or columns of transducers arranged into a square or rectangular pattern.

The first and/or the second end effector 14, 16 may be an adaptable end effector and may further comprise an acoustic coupling medium 30 and a plurality of pins 32 independently movable into and out of the first and/or second housings 22,26, as illustrated in FIGS. 2 and 3. Specifically, in some embodiments of the invention, both the first and second end effectors 14, 16 may be adaptable end effectors with the acoustic coupling medium 30 and pins 32 described herein. In other embodiments of the invention, only the first or second end effector 14, 16 may be an adaptable end effector with the acoustic coupling medium 30 and pins 32 described herein. For example, the first end effector 14 may comprise the acoustic coupling medium 30 and pins 32 described herein, as illustrated in FIG. 2, while the second end effector 16 located on a smoother surface of the part 12 may be a traditional end effector or transducer, or may simply utilize other TTU methods known in the art, as described in the Background section herein. In yet another alternative embodiments of the invention, the second end effector 16 may be omitted entirely, with various one-sided transducer methods utilized by the first end effector 14 with the adaptable end effector configuration described herein.

The acoustic coupling medium 30 may comprise a liquid, flowable solid, elastomer material, or gel. For example, the acoustic coupling medium 30 may be AQUAFLEX material manufactured by Parker Laboratories, Inc. of Fairfield, N.J. Additionally or alternatively, the acoustic coupling medium 30 may comprise a bag, pouch, or balloon with the liquid, flowable solid, elastomer material, or gel retained therein, The flowable acoustic coupling medium 30 may be thick enough to allow it to conform to local, out-of-plane variations in contour of the part 12 without being unduly stressed. For example, if local, out-of-plane contour variations protruding one inch from a global surface contour are expected on surfaces of the part 12, three inches of minimal thickness of the flowable acoustic coupling medium 30 may ensure that no part of the acoustic coupling medium 30 is compressed more than 33-percent from its nominal thickness when brought into contact with those part surfaces.

The pins 32 are configured to retain the acoustic coupling medium 30 in position directly under the transducer(s) 24,26 or linear array of transducers. Specifically, the pins 32 may each be spaced a distance apart from each other and cooperatively encircling the acoustic coupling medium 30, forming a sort of fence around the acoustic coupling medium 30. The pins 32 may move independently from one another to contact and follow local part contours of the first and/or second surfaces 34,36 of the part 12. This may ensure that the acoustic coupling medium 30 is constrained laterally within a boundary established by the pins 32. In some embodiments of the invention, the pins 32 may comprise a soft wear-resistant material having a low coefficient of friction. Additionally or alternatively, the pins 32 may include rounded tips or rolling balls configured for reducing friction while following a surface contour of the part.

In some embodiments of the invention, the pins 32 may be non-round in cross section. This may enable the pins 32 to be spaced more closely, or even touch one another, providing a more continuous confinement for the acoustic coupling medium 30. For example, the pins 32 may be trapezoidal in cross section and may be positioned in direct sliding contact with one another, thus forming a continuous wall surrounding the acoustic coupling medium 30. The pins 32 could alternatively be configured with interlocking geometries, such as dovetailed cross-sections by which one of the pins 32 would interface to adjacent pins 32. This may provide greater retention of the acoustic coupling medium 30 by the pins 32.

The pins 32 may be urged toward the first and/or second surfaces 34,36 of the part 12 by gravity, springs, resilient members, magnetism, and/or a gas or fluid pressure source coupled with the pins and configured for urging the pins 32 toward the first or second surface 34,36 of the part 12. In some embodiments of the invention, the system 10 may include a gas or fluid source and/or a pressure regulator fluidly coupled with the independently movable pins 32. Thus, the pins 32 may be urged toward the first and/or second surfaces 34,36 of the part 12 by gas or fluid pressure adjusted by the pressure regulator. Advantageously, the gas or fluid force produced may be independent of displacement, having a constant spring force.

The actuation and support components 20, as illustrated in FIG. 1, may be configured for actuating the first and second end effectors 14, 16 relative to the part 12. For example, the actuation and support components 20 may comprise rails, motors, controllers, and various electrical and communication elements for properly locating the first and second end effectors 14, 16 relative to the first surface 34 of the part 12 and the second surface 36 of the part 12. In some embodiments of the invention, at least some of the actuation and support components 20, referred to herein as fixed support components, may be configured to be fixed relative to the part, and the first and/or second housings 22,26 may be movable and/or actuatable relative to the fixed support components. Furthermore, springs and/or resilient members may physically and resiliently couple the first and/or second housings 22,26 to the fixed support components. Additionally or alternatively, a pressure regulator, gas pressure source, and/or fluid pressure source may be fluidly coupled with the first and/or second housings 22,26 in such a manner as to urge the first and/or second housings 22,26 toward the part.

In use, a method for TTU inspection may include placing the end effectors 14, 16 on the opposing surfaces 34,36 of the part 12, aligning the end effectors 14, 16 with each other, transmitting ultrasonic waves with the first end effector 14 and receiving ultrasonic waves with the second end effector 16, or vice versa. The acoustic coupling medium's volume is constrained by the pins 32, the housings 22,26, and the part surfaces 34,36, such that the acoustic coupling medium 30 is substantially incompressible and a desired average thickness of the acoustic coupling medium 30 is maintained, regardless of local variations in the first or second surface 34,36 of the part 12 during ultrasonic inspection.

Figure 4:
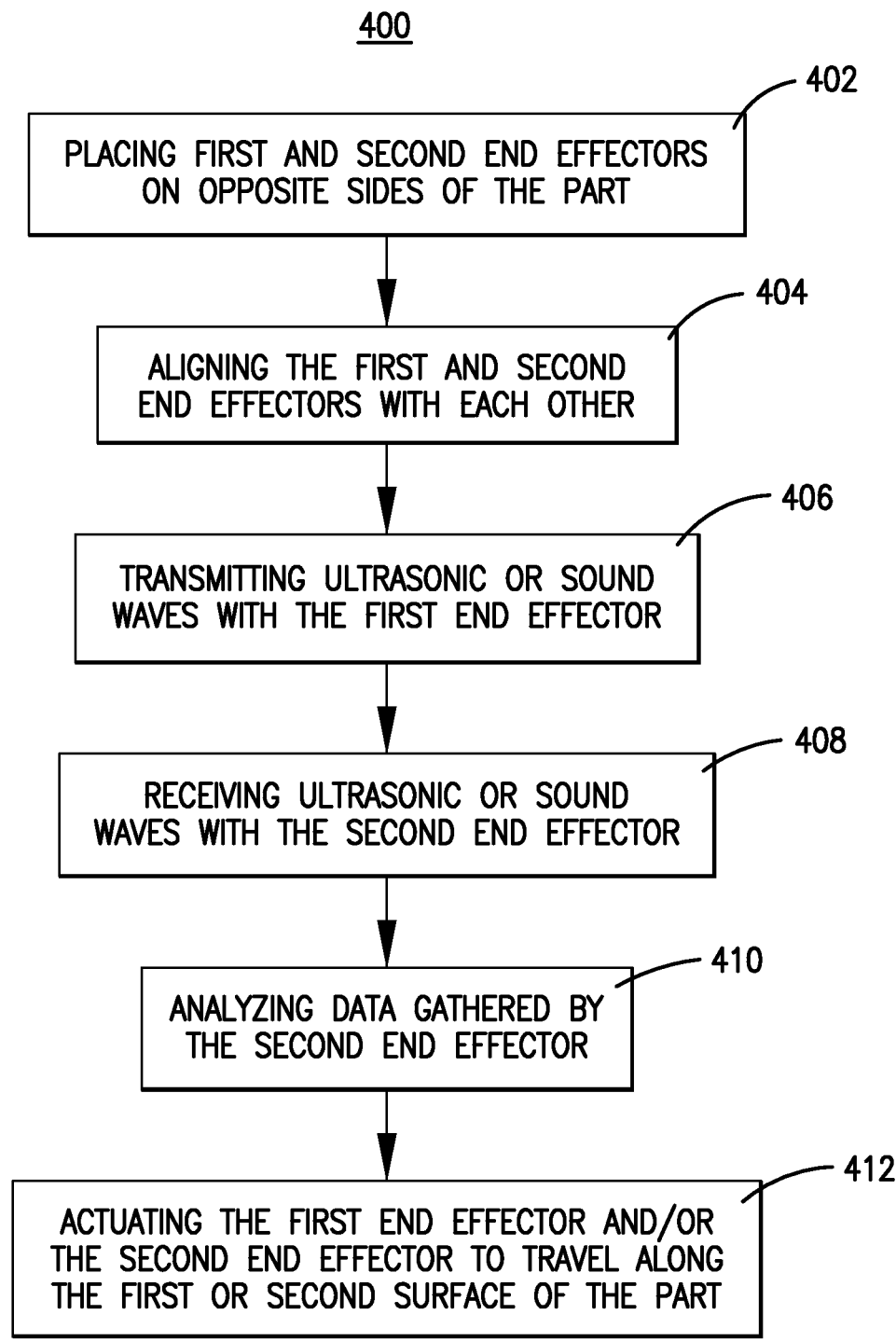
FIG. 4 is a flow chart illustrating a method of performing TTU inspection of a part in accordance with embodiments of the present invention.

Method steps for TTU inspection will now be described in more detail, in accordance with various embodiments of the present invention. The steps of the method 400 may be performed in the order as shown in FIG. 4, or they may be performed in a different order. Furthermore, some steps may be performed concurrently as opposed to sequentially. In addition, some steps may not be performed.

The method 400 may include a step of placing the end effectors 14,16 on opposite sides (e.g., the opposing surfaces 34,36) of the part 12, as depicted in block 402, and aligning the end effectors 14,16 with each other, as depicted in block 404. Initial placement of the end effectors 14,16 may be accomplished by an operator and/or some of the actuation and support components 20. Aligning the end effectors 14,16 with each other may be accomplished via associated programming to automatically properly align the end effectors 14,16, such that the transducers 24,28 properly communicate with each other through the part 12.

Force between the first and/or second end effectors 14,16 and the surfaces 34,36 of the part 12 may squeeze the acoustic coupling medium 30 between the first and/or second housings 22,26 and the first or second surfaces 34,36 of the part 12, and the acoustic coupling medium 30 is substantially incompressible. The pins 32 collectively define boundaries of the acoustic coupling medium 30 in an X-Y plane. Therefore, an average Z-direction thickness of the acoustic coupling medium 30 is constrained on all sides (i.e., a transducer side, a part side, and a boundary side defined by the pins 32), and at an average Z-direction thickness established by an amount of acoustic coupling medium 30 present. However, Z-direction thickness may not be uniform across the entire acoustic coupling medium 30, as some amount of flow can occur to accommodate local variations in surface geometry or out of plane features on the first and/or second surfaces 34,36 of the part 12. Thus, the acoustic coupling medium 30 may be thicker than its average or nominal thicknesses in the Z-direction in some areas, and thinner in others.

Next, the method 400 may include a step of transmitting ultrasonic or sound waves with the first end effector 14, as depicted in block 406, and receiving ultrasonic or sound waves with the second end effector 16, as depicted in block 408. Additionally or alternatively, the second end effector 16 may transmit ultrasonic or sound waves while the first end effector 14 receives the ultrasonic or sound waves. For example, the first transducer 24 and/or a first linear array of transducers may transmit ultrasonic or sound waves through the acoustic coupling medium 30 associated therewith and into the part 12. The ultrasonic or sound waves then move through the part 12 and to the second transducer 26 and/or a second linear array of transducers of the second end effector 16. The data gathered by the second end effector 16 may then be analyzed in any conventional manner known in the art of TTU inspection using a processor, computer, or the like, as depicted in block 410.

Finally, the method 400 may include a step of actuating the first end effector 14 and/or the second end effector 16 to travel along the first or second surface 34,36 of the part 12, as depicted in block 412. While traveling along the surfaces 34,36 of the part 12, the pins 32 may independently slide toward and away from the first or second housing 22,26, accommodating local variations in surface geometry or out-of-plane features of the part 12. This actuation may move the first and second end effectors 14,16 to different areas of interest on the part 12 and/or may be required during alignment procedures.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

The invention claimed is:

1. An ultrasonic inspection system for ultrasonic inspection of a part, the system comprising:
   a first end effector having:
      a first housing;
      at least one transducer fixed to the first housing, wherein the at least one transducer is configured to transmit ultrasonic or sound waves through the part;
      an acoustic coupling medium; and a plurality of pins coupled with the first housing and independently movable toward and away from the first housing, the pins cooperatively encircling the acoustic coupling medium.

2. The system of claim 1, wherein the acoustic coupling medium comprises at least one of:
a liquid, flowable solid, elastomer material, or gel, and
a bag, pouch, or balloon with the liquid, flowable solid, elastomer material, or gel retained therein.

3. The system of claim 1, further comprising at least one of springs, resilient members, and a gas or fluid pressure source coupled with the pins and configured for urging the pins toward a surface of the part.

4. The system of claim 1, further comprising a pressure regulator fluidly coupled with the pins and configured to produce independent displacement of the pins at a constant spring force.

5. The system of claim 1, further comprising a second end effector having a second housing and at least one transducer fixed to the second housing and configured to receive from the first end effector the ultrasonic or sound waves after they pass through the part.

6. The system of claim 1, wherein the pins comprise a soft wear-resistant material having a low coefficient of friction.

7. The system of claim 1, wherein the pins include rounded tips or rolling balls configured for reducing friction while following a surface contour of the part.

8. The system of claim 1, wherein the at least one transducer may include a linear array of transducers configured to at least one of send and receive ultrasonic waves through the part.

9. The system of claim 1, further comprising actuation and support components configured for actuating the first and second end effectors relative to the part.

10. A through-transmission ultrasonic (TTU) inspection system for ultrasonic inspection of a part, the system comprising:
a first end effector having a first housing and at least one transducer fixed to the first housing and configured to send or receive ultrasonic waves; and
a second end effector having a second housing and at least one transducer fixed to the second housing and configured to send or receive ultrasonic waves,
wherein at least one of the first end effector and the second end effector further comprises:
an acoustic coupling medium, and
a plurality of pins coupled with the housing and independently movable into and out of the first housing, the pins cooperatively encircling the acoustic coupling medium.

11. The system of claim 10, wherein the acoustic coupling medium comprises at least one of:
a liquid, flowable solid, elastomer material, or gel, and
a bag, pouch, or balloon with the liquid, flowable solid, elastomer material, or gel retained therein.

12. The system of claim 10, further comprising at least one of springs, resilient members, and a gas or fluid pressure source coupled with the pins and configured for urging the pins toward a surface of the part.

13. The system of claim 10, further comprising a pressure regulator fluidly coupled with the pins and configured to produce independent displacement of the pins at a constant spring force.

14. The system of claim 10, further comprising at least one of springs, resilient members, and a gas or fluid pressure source coupled with the first housing and configured for urging the first housing toward a surface of the part.

15. The system of claim 10, wherein the pins comprise a soft wear-resistant material having a low coefficient of friction.

16. The system of claim 10, wherein the pins include rounded tips or rolling balls configured for reducing friction while following a surface contour of the part.

17. The system of claim 10, wherein the transducers may include linear arrays of transducers configured to at least one of send and receive ultrasonic waves through the part.

18. The system of claim 10, further comprising actuation and support components configured for actuating the first and second end effectors relative to the part.

19. A method for inspecting a part having a first surface and a second surface opposite of the first surface using through-transmission ultrasonic (TTU) inspection, the method comprising the steps of:
placing a first end effector against the first surface of the part, wherein the first end effector comprises a first housing and an array of transducers fixed to the first housing and configured to send or receive ultrasonic waves;
placing a second end effector against the second surface of the part in alignment with the first end effector, wherein the second end effector has a second housing and an array of transducers fixed to the second housing and configured to send or receive ultrasonic waves; and
transmitting ultrasonic waves with the transducers of the first end effector; and
receiving ultrasonic waves with the transducers of the second end effector,
wherein at least one of the first end effector and the second end effector further comprises:
an acoustic coupling medium including:
a liquid, flowable solid, elastomer material, or gel, or
a bag, pouch, or balloon with the liquid, flowable solid, elastomer material, or gel retained therein, and
a plurality of pins independently movable into and out of the first or second housing, and cooperatively encircling the acoustic coupling medium.

20. The method of claim 19, further comprising actuating at least one of the first end effector and the second end effector to travel along the first or second surface of the part, such that the plurality of pins independently slide toward and away from the first or second housing, accommodating local variations in surface geometry or out-of-plane features of the part.

* * * * *